(12) United States Patent
Rosenbaum et al.

(10) Patent No.: US 6,584,430 B1
(45) Date of Patent: Jun. 24, 2003

(54) SYSTEM AND METHOD FOR DEVICE MONITORING

(75) Inventors: Rafi Rosenbaum, Givataim (IL); Shaul Shohat, Petach-Tikva (IL); Rakefet Fish, Ramat Gan (IL); Judith Kessler, Rehovot (IL); Lazars Kupeli, Danville, CA (US)

(73) Assignee: Bio Rad Laboratories, Inc., Hercules, CA (US)

( * ) Notice: Subject to any disclaimer, the term of this patent is extended or adjusted under 35 U.S.C. 154(b) by 0 days.

(21) Appl. No.: 09/119,148

(22) Filed: Jul. 20, 1998

(30) Foreign Application Priority Data

Jul. 21, 1997 (IL) .................................................. 121348

(51) Int. Cl.[7] ........................... G06F 11/30; G06F 15/00
(52) U.S. Cl. ....................................... 702/183; 340/641
(58) Field of Search ........................ 702/23–32, 81–84, 702/182, 183–186, 188; 706/60, 45, 48, 50, 62; 709/201; 340/635, 641; 204/451

(56) References Cited

U.S. PATENT DOCUMENTS

| 4,254,472 A | * | 3/1981 | Juengel et al. .............. 702/188 |
| 4,654,512 A | * | 3/1987 | Gardosi ....................... 235/376 |
| 4,667,509 A | * | 5/1987 | Tobolski et al. ................ 73/83 |
| 4,816,994 A | * | 3/1989 | Freiling et al. ................ 706/11 |
| 5,025,391 A | * | 6/1991 | Filby et al. .................... 706/45 |
| 5,428,470 A | * | 6/1995 | Labriola, II .................. 359/119 |
| 5,608,845 A | * | 3/1997 | Ohtsuka et al. ............... 702/34 |
| 5,812,529 A | * | 9/1998 | Czarnik et al. ............. 370/245 |
| 6,049,764 A | * | 4/2000 | Stahl .......................... 702/183 |

OTHER PUBLICATIONS

Cassel et al. Management of Distributed Measurement over Interconnected Networks Mar. 1988. IEEE Networks. pp 50–56.*

Grimaldi et al. Java Based Distributed Measurement Systems May 19–21, 1997. IEEE Instrumentation and Measurement Technology Conference. pp 686–688.*

Giarrantano et al. Expert Systems: Principles and Programming. 1994. pp. 578–594.*

* cited by examiner

Primary Examiner—Marc S. Hoff
Assistant Examiner—Manuel L. Barbee
(74) Attorney, Agent, or Firm—Mark M. Friedman

(57) ABSTRACT

A system for monitoring the state and performance of an analysis device, such as a capillary electrophoresis instrument. The system includes software for operating the analysis device and system management software for monitoring the device, generating a report on the state of the device and selecting an appropriate response based on this report. The response can include altering the function of one or more parts of the device, or signaling the need for a repair to be performed, for example.

1 Claim, 8 Drawing Sheets

SYSTEM AND METHOD FOR DEVICE MONITORING

FIELD AND BACKGROUND OF THE INVENTION

The present invention relates to a system and a method for monitoring analysis devices and, in particular, it concerns a system and a method for diagnosing operating faults, adjusting operating parameters and providing routine maintenance for such devices.

Many different types of analysis devices are used for scientific and medical analysis in a laboratory setting. As these devices have become increasingly sophisticated, many now require complex software for their operation. Although such software can provide a simple and user-friendly interface for the routine operation of the device, difficulties arise when operating parameters must be changed, or when the operating software must be upgraded. Many of these adjustments are relatively routine, yet can be difficult and complicated for all but the most sophisticated user. Thus, routine maintenance has become extremely complex for such devices.

Furthermore, should the device itself actually experience operating faults, such that the performance of the device is reduced, the average user may not be aware that a problem has arisen. Even if the device is clearly inoperative, the average user would not be able to diagnose the problem, so that a repair technician would need to travel to the laboratory to assess the device. Should a new part be required, further visits to the laboratory would be necessary to obtain the part and then repair the device. Thus, on-site repair currently can require multiple visits and result in a relatively long period in which the device cannot be used, both of which are very costly and frustrating for the user.

There is therefore an unmet need for, and it would be highly advantageous to have, a system and a method for remotely monitoring the performance of an analysis device, diagnosing any problems and performing routine maintenance with a minimum of human intervention.

SUMMARY OF THE INVENTION

According to the teachings of the present invention, there is provided a system for monitoring an analysis device, comprising: (a) an instrument software for operating the analysis device; and (b) a system management software for receiving a report of a state of the analysis device from the instrument software and for determining a response to the report, the system management software including: (i) a hardware monitoring agent for interacting with the instrument software to obtain the report; and (ii) an expert system software for determining if the report is of an instrument error state, and for recommending an error correction response if the report is of the instrument error state.

Preferably, the response includes a command to alter at least one operating parameter of the analysis device. Also preferably, the command is sent to the instrument software by the hardware monitoring agent and is executed by the instrument software. Optionally, the response is an alarm to warn a user of the analysis device. Alternatively and preferably, the response includes ordering a component of the analysis device from a service provider.

According to another preferred embodiment of the present invention, the instrument software is run on a first computer connected locally to the analysis device and the system management software is run on a second computer connected remotely to the analysis device. Preferably, the system management software allows the analysis device to be adjusted by the second computer through the instrument software.

According to a preferred embodiment of the present invention, the expert system software includes: (a) an expert system model module for containing a list of instrument error states and a list of corresponding tests to perform; (b) an expert system engine module for determining the response based on the list of error states and on the list of corresponding tests; and (c) an expert system log module for recording interactions between the expert system software and the instrument software. Preferably, the expert system engine module further selects a test to be performed on the analysis device and the hardware monitoring agent performs said test through said instrument software. Also preferably, the expert system software further analyzes said recorded interactions between said expert system software and said instrument software in order to add information to said expert system model module.

According to another embodiment of the present invention, there is provided a method of diagnosing an operating fault in an analysis device, comprising the steps of: (a) providing the analysis device with an instrument software for operating the analysis device; (b) obtaining a report of the operating fault from the instrument software; (c) selecting a command to correct the operating fault based upon said report; and (d) causing said instrument software to execute said command to correct the operating fault.

According to yet another embodiment of the present invention, there is provided a system for the maintenance of an analysis device, including: (a) an instrument software for operating the analysis device; and (b) a system management software for determining when a maintenance action is to be performed on the analysis device. Preferably, the maintenance action includes determining when a component of the analysis device should be replaced. Also preferably, the maintenance action includes an automatic adjustment of an operating parameter of the analysis device.

BRIEF DESCRIPTION OF THE DRAWINGS

The invention is herein described, by way of example only, with reference to the accompanying drawings, wherein.

DESCRIPTION OF THE INVENTION

Figure 1:
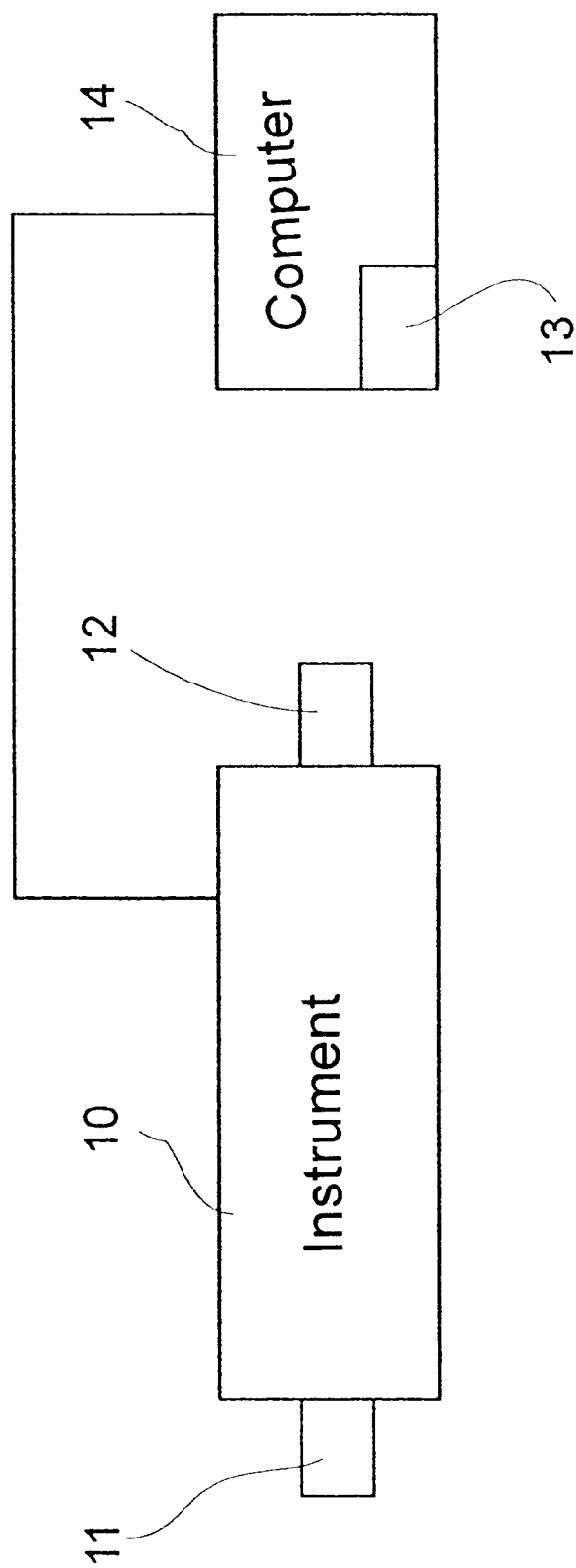
FIG. 1 is a schematic illustration of a prior art analysis device.

The present invention is of a method and a system for performing routine maintenance, diagnosing problems and preferably upgrading software for one or more analysis devices.

As used herein, the term "analysis device" refers to any device for performing a scientific or medical analysis, including both research laboratory instrumentation and instruments used for clinical diagnostic procedures, as well as any process monitoring device. For example, the analysis device could measure the level of glucose in a blood sample taken from a patient. Typically such devices include a sample input such as a chamber into which the blood sample is inserted. These devices also include an analysis module which would actually perform the analysis, for example by determining the concentration of glucose in the blood sample. If necessary, one or more reagents are added to the sample when in contact with the analysis device. Finally, the results of the analysis are displayed or given to the user in some form.

As these analysis devices have become more complicated, their routine operation has been increasingly performed by software on a computer either attached to, or included with, the analysis device, hereinafter referred to as the "instrument computer". Such software has the advantage of simplifying routine operation of the device, as well as of being able to store, format and display the results in many different ways. However, many functions must still be performed either by the user or by a skilled repair technician.

In an effort to reduce the number of functions which must be performed either by the user or by a skilled repair technician, an overall system of monitoring and, if necessary, intervening in the function of the analysis device through the operating software would be useful. The system of the present invention includes software for system management, hereinafter referred to as the "system management software", which can interact with the software which operates the analysis device. Through this interaction, the system management software can either monitor the performance of the analysis device, adjust one or more operating parameters of the analysis device, or both, as well as optionally provide assistance to the user through on-line help manuals, for example.

Optionally, the system of the present invention can also include a connection, via the Internet, to a monitoring computer at a remote location. Hereinafter, the term "Internet" is used to generally designate the global, linked web of thousands of networks which is used to connect computers all over the world. As used herein, unless otherwise indicated, the term "Internet" can also include other types of networks, such as LAN (local area networks) or WAN (wide area networks), it being understood that the term "network" includes any connection between at least two computers. Hereinafter, the term "local" includes any site where the analysis device is located, such as a laboratory, a company, a hospital or a university. The term "remote" refers to any other separate site.

Such an Internet connection can either be substantially continuous or intermittent. With this connection, information which is available on the network computers can be directly downloaded to the instrument computer. Such information can include reference information such as user manuals and product information. Optionally, products could be ordered from a product source, such as a service provider, via the Internet. Also optionally, a service provider could directly monitor the performance of the analysis device through the system management software, to aid in the detection of operating faults or for routine maintenance of the system. Such monitoring could be particularly invaluable when planning service calls to the laboratory by repair technicians, either for routine maintenance or to repair an inoperative or faulty analysis device.

Furthermore, new or improved data about the analysis device could also be given to the instrument computer in the form of updated operating parameters. Such updated operating parameters would then be used by the system management software to adjust the operation of the instrument computer in order to obtain a greater level of performance. Currently, each individual user must manually adjust the analysis device to compensate for factors such as differences between production lots of reagents. Enabling the system management software to perform such adjustments automatically significantly increases the efficiency of the analysis device and frees the user from performing such adjustments manually.

In addition, both software initial installations and upgrades can optionally be performed through the system management software. Hereinafter, the term "initial installation" refers to the addition of software to the computer for the first time, without previous versions of the software being available on the computer. The term "software upgrade" refers to the addition of new features or patches for known problems to software already installed on the computer.

It is envisioned that all of these services could be performed through a service provider, which would give technical support and advice, perform maintenance and repairs on the analysis device, act as a vendor for related products and generally provide needed support to the user of the analysis device.

All of the functions of the system management software may be performed either automatically, semi-automatically, or both. Hereinafter the term "automatic" refers to the performance of a function substantially without user intervention or input, while the term "semi-automatic" refers to the performance of a function with at least partial user intervention or input required for one or more steps.

DESCRIPTION OF THE PREFERRED EMBODIMENTS

The present invention is of a method and a system for monitoring analysis devices, for diagnosing operating faults in these devices, and for adjusting operating parameters of the devices. As noted previously, the system includes at least one analysis device which is operated by instrument software running on a computer, and system management software which interacts with the instrument software to monitor the analysis device. Optionally, the system also includes a connection to one or more computers via the Internet.

The principles and operation of a method and a system according to the present invention may be better understood with reference to the drawings and the accompanying description. Referring now to the drawings, FIG. 1 shows a prior art analysis device as an example of such a device. Although the present invention will be described in terms of this specific analysis device, a capillary electrophoresis instrument, it is understood that this is for illustrative purposes only and is not meant to be limiting in any way. A capillary electrophoresis instrument system includes a capillary electrophoresis instrument 10. Capillary electrophoresis instrument 10 includes a sample input 11 which preferably holds multiple samples. The user places one or more samples in sample input 11. Next, a portion of the sample is automatically placed within an analysis module 12 of capillary electrophoresis instrument 10. Analysis module 12 includes a capillary into which the portion of the sample is placed (not shown). A voltage is applied across this capillary, causing various components of the sample, such as proteins, to become separated (not shown). The results of the separation are given as one or more peaks, defining a relative concentration of each component within the sample (not shown). Preferably, the results are analyzed and displayed on a video monitor screen of a computer as described below.

The capillary electrophoresis instrument system also includes instrument software 13 to operate capillary electrophoresis instrument 10, and an instrument computer 14 on which instrument software 13 is run. For the sake of clarity, FIG. 1 shows instrument software 13 on instrument computer 14. Instrument software 13 can include one or more separate programs or modules. Optionally, one or more functions of capillary electrophoresis instrument 10 are performed automatically by instrument software 13. Instrument software 13 also enables the user to set one or more operating parameters of capillary electrophoresis instrument 10, such as the amount of one or more reagents to be added to the sample if necessary. Generally, instrument software 13 has substantially all the functions which are required to enable the user to operate capillary electrophoresis instrument 10. Preferably, the user would not need to directly manipulate one or more portions of capillary electrophoresis device 10, as these manipulations should be performed via instrument software 13. Instrument software 13 also analyzes the results obtained from analysis module 12 and places them in a suitable format for display on the monitor of instrument computer 14.

Figure 2:
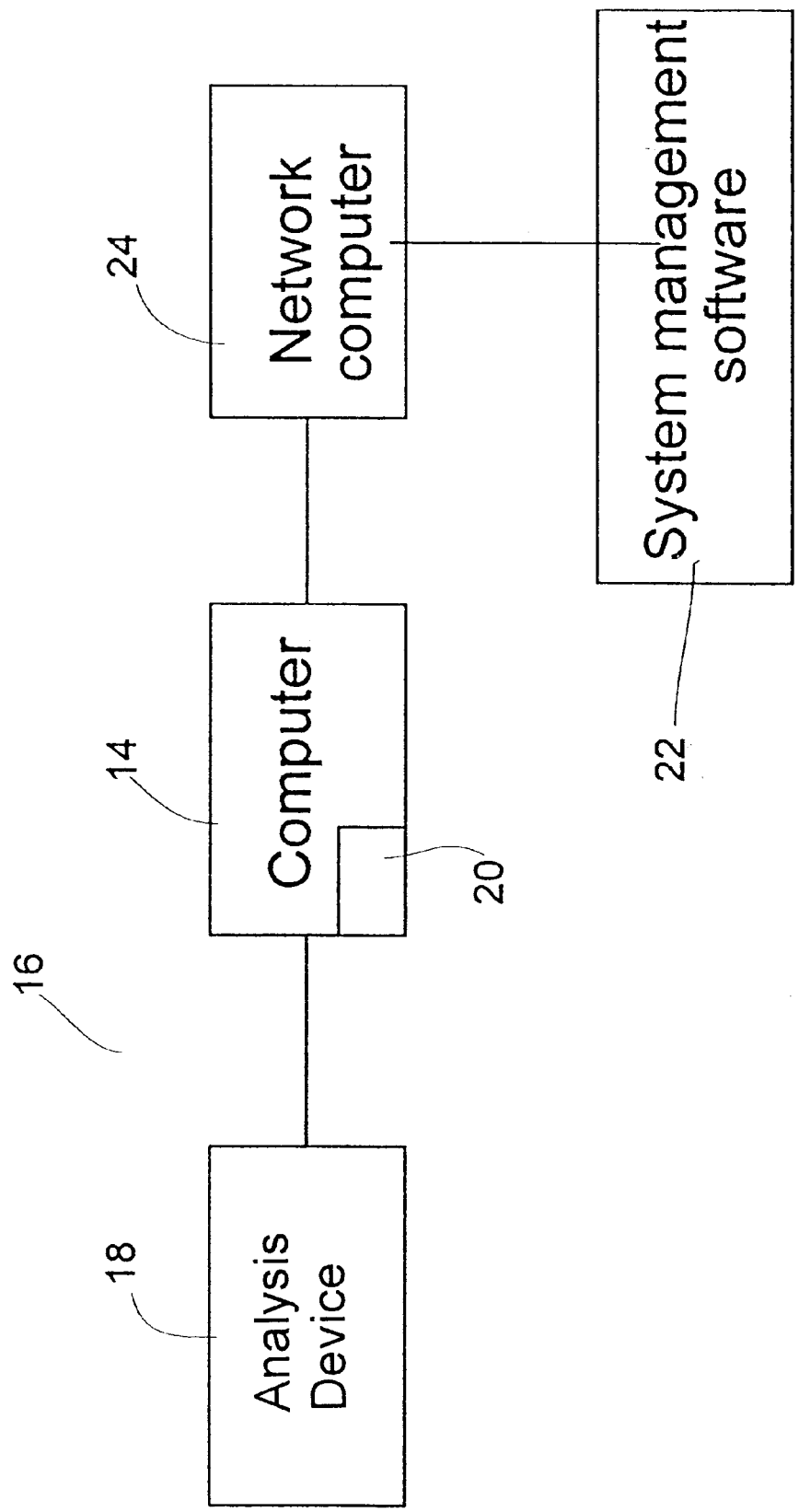
FIG. 2 is a schematic illustration of an instrument monitoring system according to the present invention.

FIG. 2 shows an instrument monitoring system according to the present invention. An instrument monitoring system 16 includes an analysis device 18 with instrument software 20. Analysis device 18 performs one or more analysis functions, preferably for scientific or medical analysis as shown in the prior art device of FIG. 1.

System management software 22 is able to interact with instrument software 20. System management software 22 can be installed on computer 14, analysis device 18 or on a network computer 24 as shown. System management software 22 is able to interact with instrument software 20 to perform a number of functions generally included under the phrase "monitoring of analysis device".

First, system management software 22 can simply monitor the function of analysis device 18, such as passively examining analysis results, measuring reagent levels and determining the relative level of background noise being generated by analysis device 18 or by the samples themselves.

Second, system management software 22 can actively intervene in the routine function of analysis device 18 and perform a maintenance action, for example by adjusting one or more operating parameters. Such operating parameters include, but are not limited to, the amount of any necessary reagents and factors which influence background noise. Other examples of maintenance actions include determining when a component of the analysis device should be replaced, such as a lamp which has reached the end of its expected operating life.

Third, system management software 22 preferably can diagnose operating faults and problems, including but not limited to lack of a required reagent, lack of a sufficient sample volume, incorrect adjustment of one or more parts within analysis device 18 such as the sample input, or the presence of a faulty part such as a burnt-out light source, for example.

The fourth function of system management software 22, performing software installation and upgrades, is preferably performed in conjunction with network computer 24. Network computer 24 is an optional but preferable feature of system 16. Network computer 24 is connected to computer 14 via a network connection such as the Internet. Network computer 24 can include a database with information as described previously, or new or upgraded software, which can be downloaded to computer 14. Such downloading, and the subsequent installation of any programs, is preferably performed by system management software 22.

Figure 3:
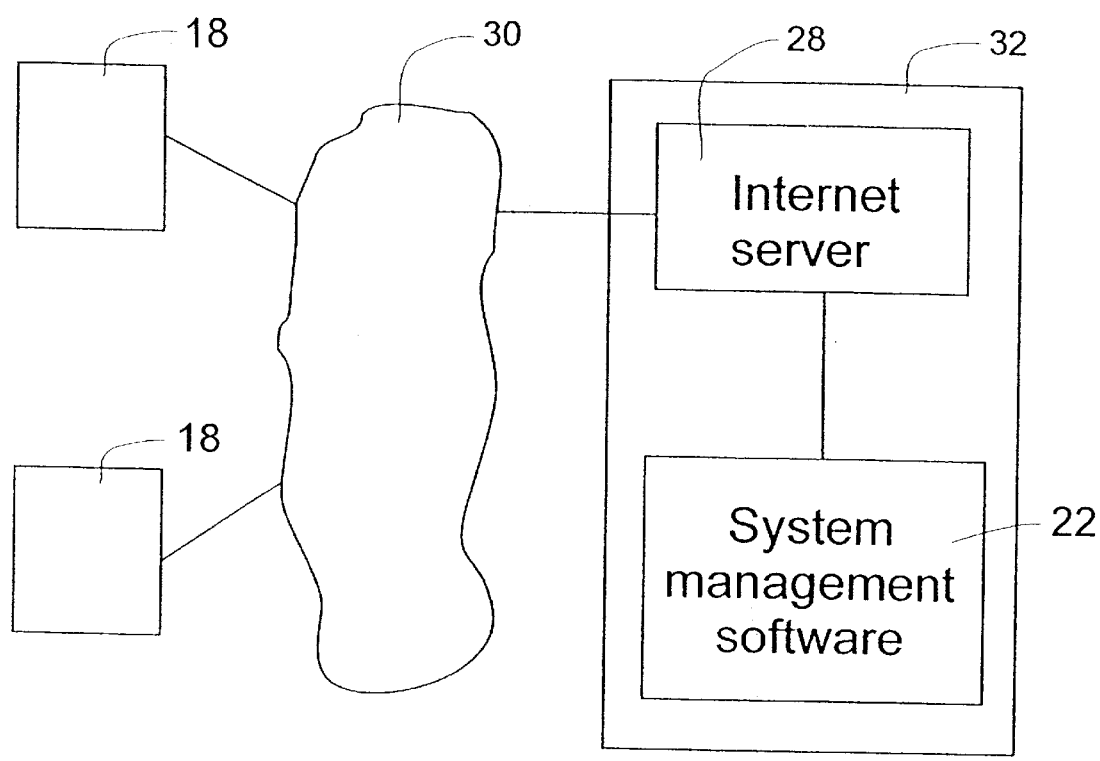
FIG. 3 diagrams one embodiment of the present invention showing interactions with a service provider.

FIG. 3 illustrates an expanded version of the network computer and network connection of FIG. 2 according to a preferred embodiment of the present invention. Here, multiple analysis devices 18 are connected to an Internet server 28 via the Internet 30. Internet server 28 in turn is a gateway to a service provider 32 which can be at a remote location, including a completely different country. Service provider 32 provides services related to the routine maintenance and repair of analysis device 18, and optionally provides a number of other services, such as answering any questions of the user about analysis device 18, automatically reminding the user about the need to order further quantities of any necessary reagents, and even monitoring the performance of analysis device 26. For these latter optional services, service provider 32 should preferably operate system management software 22. Such an expanded network connection can enable the user to benefit from such services without requiring an on-site visit by a technician from service provider 32. Furthermore, even if an on-site visit is required, the number and duration of such visits can potentially be reduced by the Internet connection.

Preferably, service provider 32 is connected to Internet server 28 through a firewall for added security (not shown).

Figure 4:
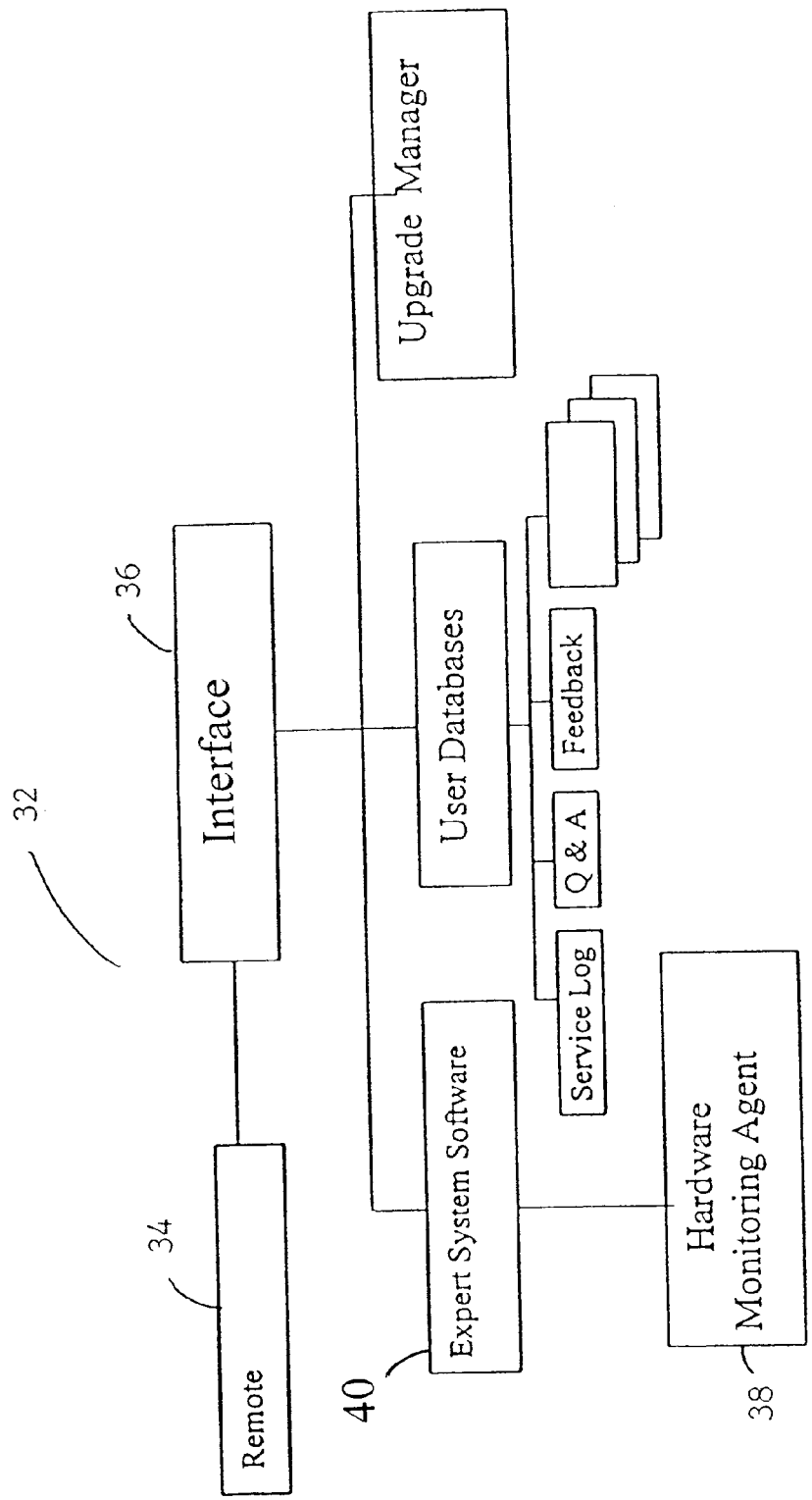
FIG. 4 is a more detailed diagram of the system management software of the present invention.

FIG. 4 illustrates one possible embodiment of the service provider system of FIG. 3. In this embodiment, a remote user 34 connects to system management software 22 via an user interface 36. Preferably, user interface 36 is a "home page" accessible by a web browser. Hereinafter, the term "web browser" includes any software program which can interact with a web server to display documents written in HTML (HyperText Mark-up Language). The term "home page" or "web page" includes any such HTML document.

One advantage of using a "home page" for user interface 36 is that context-sensitive messages can easily be added to the "home page" for the user to view. Such context-sensitive messages are well known in the art, and are typically used for advertising and the like, although of course the message could have substantially any content. These messages are preferably selected for their content depending upon the actions of the user. For example, if the user were asking for product information, an advertisement by the company which manufactured that product could appear as the context-sensitive message. Many other examples of such context-sensitive messages, and the context in which they are selected, would occur to one of ordinary skill in the art. Furthermore, even if user interface 36 uses some other GUI (graphical user interface) technology, such context-sensitive messages could easily be displayed using that technology. Optionally, the particular context could be obtained from instrument software 20 and sent to system management software 22. Preferably, the context-sensitive message would then be displayed by instrument software 20.

User interface 36 enables the user to connect indirectly to a hardware monitoring agent 38. However, hardware monitoring agent 38 is also preferably connected separately to the analysis device of remote user 34, for example via a separate Internet connection. Hardware monitoring agent 38 monitors instrument software 20 at least intermittently, for example at the request of remote user 34, but preferably constantly. Hardware monitoring agent 38 performs such monitoring by looking for pre-defined sets of instrument status codes.

An instrument status code is a code produced by instrument software 20 which describes the state of the analysis device, such as whether the device is waiting for a command, in a power-saving mode or performing an analysis. Certain of these codes indicate states in which the performance of the analysis device is either reduced or eliminated because of a problem within the analysis device, and can be described as an error code. Hardware monitoring agent 38 initiates a fault detection session when such an error code is detected, or even when a particular combination of instrument codes indicates that a problem may be present. A fault detection session can also be initiated by a user request. Once such a session is initiated, hardware monitoring agent 38 connects to, and interacts with, expert system software as shown in FIG. 5.

Figure 5:
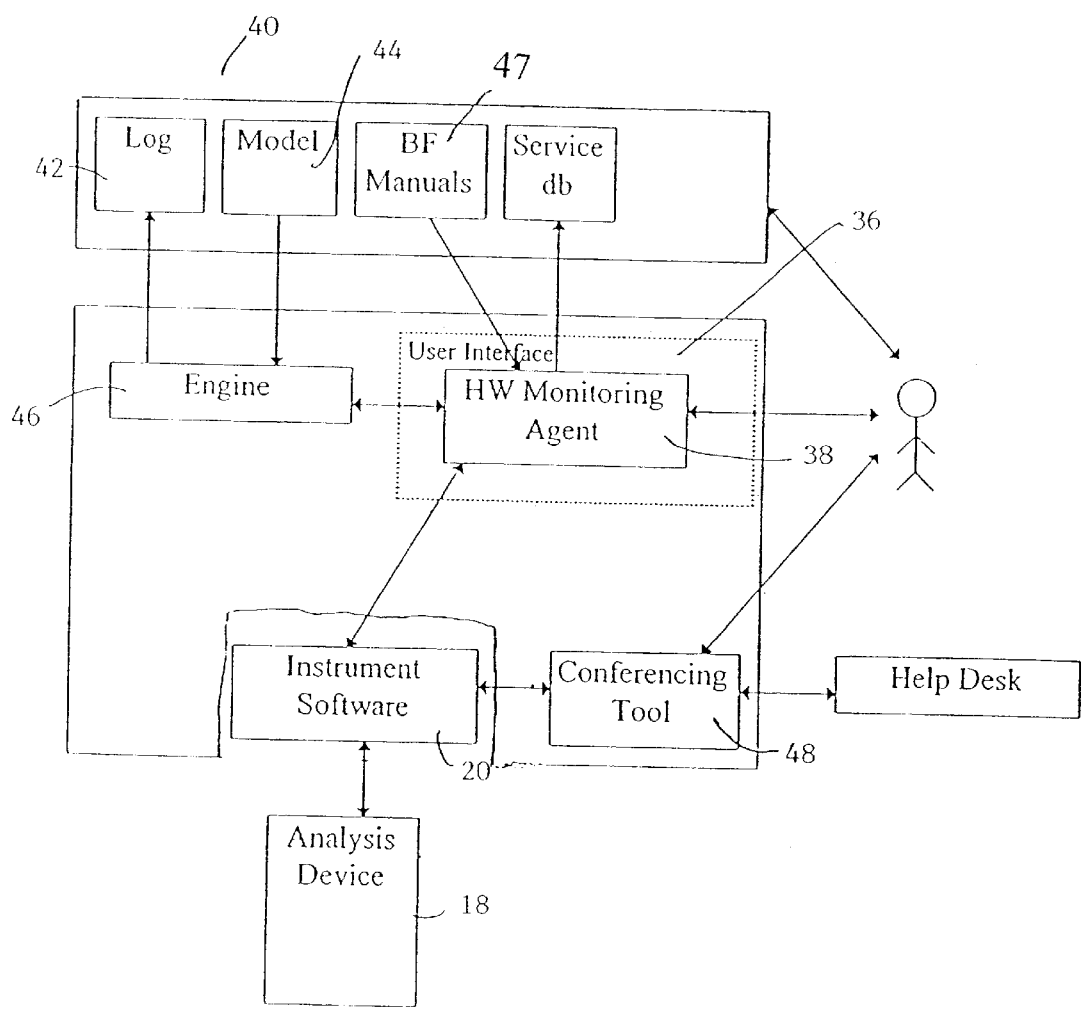
FIG. 5 shows one example of the relationship between the hardware monitoring agent of the present invention and other components of the system management software of the present invention.

FIG. 5 shows one particular embodiment of the relationship between the instrument software and the hardware monitoring agent. The user interacts with hardware monitoring agent 38 through user interface 36. Hardware monitoring agent 38, either automatically or according to a request of the user, interacts with the three components of an expert system software 40: expert system log module 42, expert system model module 44 and expert system engine module 46. These interactions enable hardware monitoring agent 38 to perform various monitoring functions and repairs.

Expert system model module 44 contains a schematic description of analysis device 18, including any necessary technical information; a definition of tests that can be performed on analysis device 18; and a list of faulty symptoms and the underlying problem or problems which generate them. Expert system log module 42 records a description of all interactions between expert system software 40 and instrument software 20. Expert system engine module 46 interacts with instrument software 20 through hardware monitoring agent 38 to request to perform a test as described in expert system model module 44. Hardware monitoring agent 38 then performs the test either directly through instrument software 20 or via interaction with the remote user. The results are then transferred back to expert system software 40. This process continues until expert system software 40 reaches a conclusion on the faulty element.

As its name suggests, the various components of expert system software 40 together form an "expert system", which are well known in the art. Such a system is capable of using information supplied by the user, such as the basic configuration of the components of analysis device 18, types of diagnostic tests, interpretation of error codes and interpretation of test results. This information constitutes a model of analysis device 18. This model is then placed within expert system model module 44. Next, expert system engine module 46 then uses the model of expert system model module 44, in combination with information from instrument software 20, to diagnose any problems with the performance of analysis device 18. All interactions are then recorded by expert system log module 42 so that expert system software 40 can actually "learn", or incorporate new data into expert system model module 44 in order to improve its diagnostic ability.

Of course, the exact performance of expert system software 40 will depend upon its location relative to the user.

When instrument software 20 is running on the same computer as system management software 22, automatic hardware monitoring and testing is possible. In this case, the state of analysis device 18 is monitored continuously. Fault states and problematic parameter values ("symptoms") will trigger a fault diagnosis session using expert system software 40 according to the procedure outlined above. In addition, if the user detects a problem, the user can manually switch to system management software 22 and activate hardware monitoring agent 38. This should both reduce the need for service calls, and make service calls more efficient by supplying better descriptions of problems.

If the fault cannot be isolated with automatic tests, then further testing requiring user intervention may be performed. Instructions from a multimedia user/service manual 47 for user-assisted tests are displayed, and the user can report the results. Expert system software 40 then reports suspect components the defective device if the fault has been completely isolated. The user will also be able to confirm the diagnosis, or enter the actual faulty component if the expert system software diagnosis was incorrect.

An optional feature of hardware monitoring agent 38 is the ability to recommend or initiate routine maintenance. Hardware monitoring agent 38 optionally features a database which includes a list of parts which have known expected lifetimes, and the installation date of those parts in analysis device 18. When the age of a part is close to its expected life, hardware monitoring agent 38 signals the service provider to schedule a preventive maintenance service call which will include replacing this part. In addition other conditions can be defined which signal that preventive maintenance is needed.

Should hardware monitoring agent 38 prove unable to solve the problem, the user can contact a service technician for additional help in isolating and solving the problem through a conferencing tool 48. Conferencing tool 48 allows the service technician to see all the information on the monitor screen of the user's computer. Preferably, conferencing tool 48 includes an audio device for two-way communication between the user and the service technician, or even a video device for visual communication (not shown). Preferably, conferencing tool 48 also allows the service technician to manipulate the user's computer from a remote location.

In addition, optionally and preferably the user will be able to obtain information about the various components of system management software 22, instrument software 20 or even analysis device 18 through an on-line manual 47. On-line manual 47 includes multi-media content such as video, audio, images and drawings. The content of on-line manual 47 will include information on symptoms, tests, maintenance procedures and service procedures defined in expert system model 44, as well as information generally included in user's manual, such as protocols for operating analysis device 18.

Figure 6:
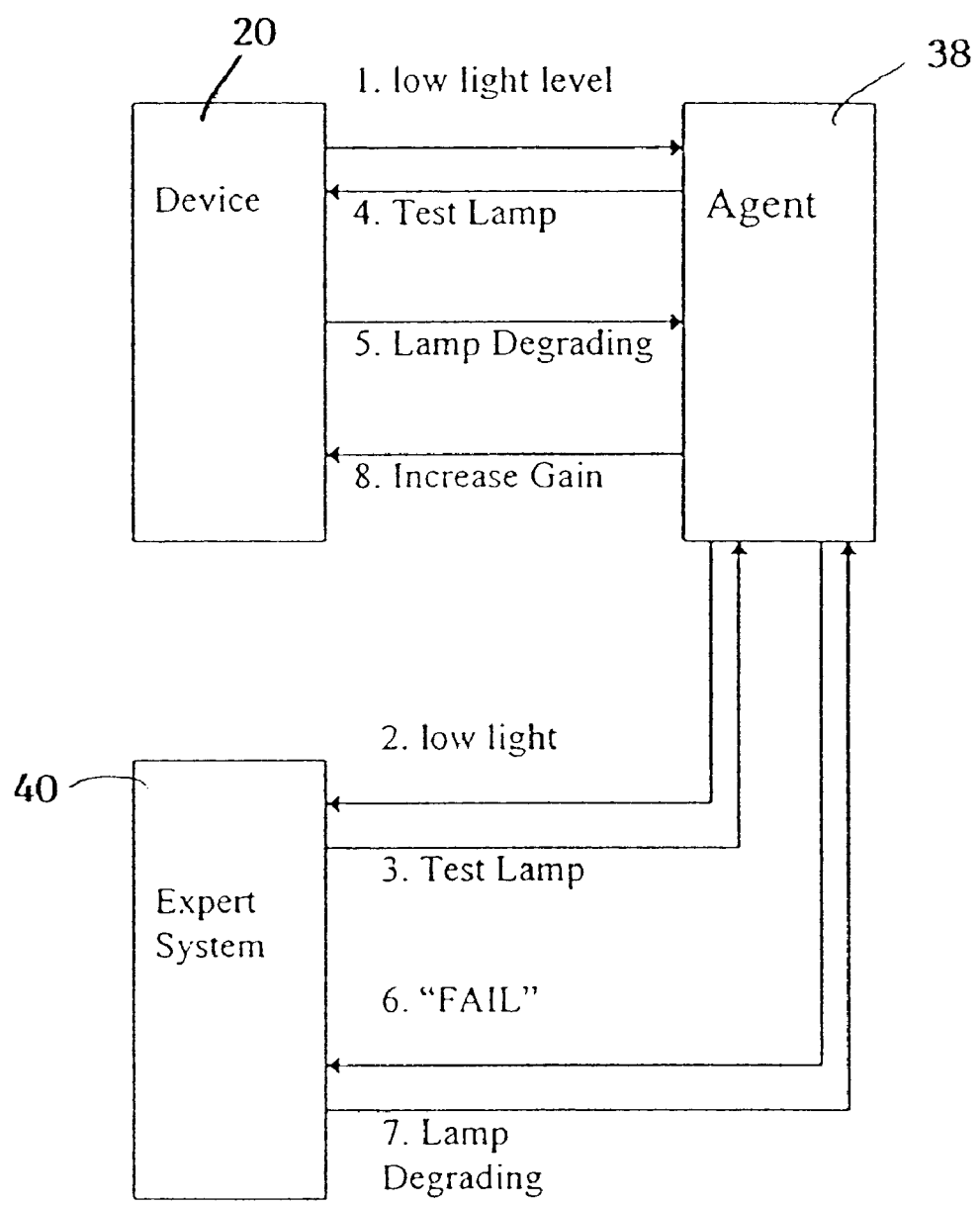
FIG. 6 illustrates one example of a fault diagnosis scenario.

FIG. 6 describes an example of a fault locating session with the expert system software and the instrument software. The analysis device being examined could be the capillary electrophoresis instrument of FIG. 1, for example.

In the first step, shown as "1" on the diagram, a symptom is entered either by the user or automatically by instrument software 20: the lamp light level is low. Hardware monitoring agent 38 then interacts with expert system software 40, sending the symptom as shown in step 2. Expert system software 40 then sends the recommendation to test the lamp by checking to see if the lamp performance is degrading, as shown in step 3. Hardware monitoring agent 38 then interacts with the user through instrument software by requesting the user to test the lamp condition, as shown in step 4. Alternatively, hardware monitoring agent 38 could directly pass the command to instrument software 20.

Instrument software 20 gives the result that the lamp is degrading to hardware monitoring agent 38 as shown in step 5. Hardware monitoring agent 38 then passes the result "FAIL" to expert system software 40 as shown in step 6. Expert system software 40 then identifies the lamp as the faulty unit to hardware monitoring agent 38, as shown in step 7. Hardware monitoring agent 38 then instructs instrument software 20 to display an explanation for the user of how to increase the gain to compensate and correct the problem, as shown in step 8. Alternatively, hardware monitoring agent 38 could directly instruct instrument software 20 to increase the gain. Optionally, the user could also be warned that a new lamp should be ordered soon. Preferably, the order is placed automatically.

Figure 7:
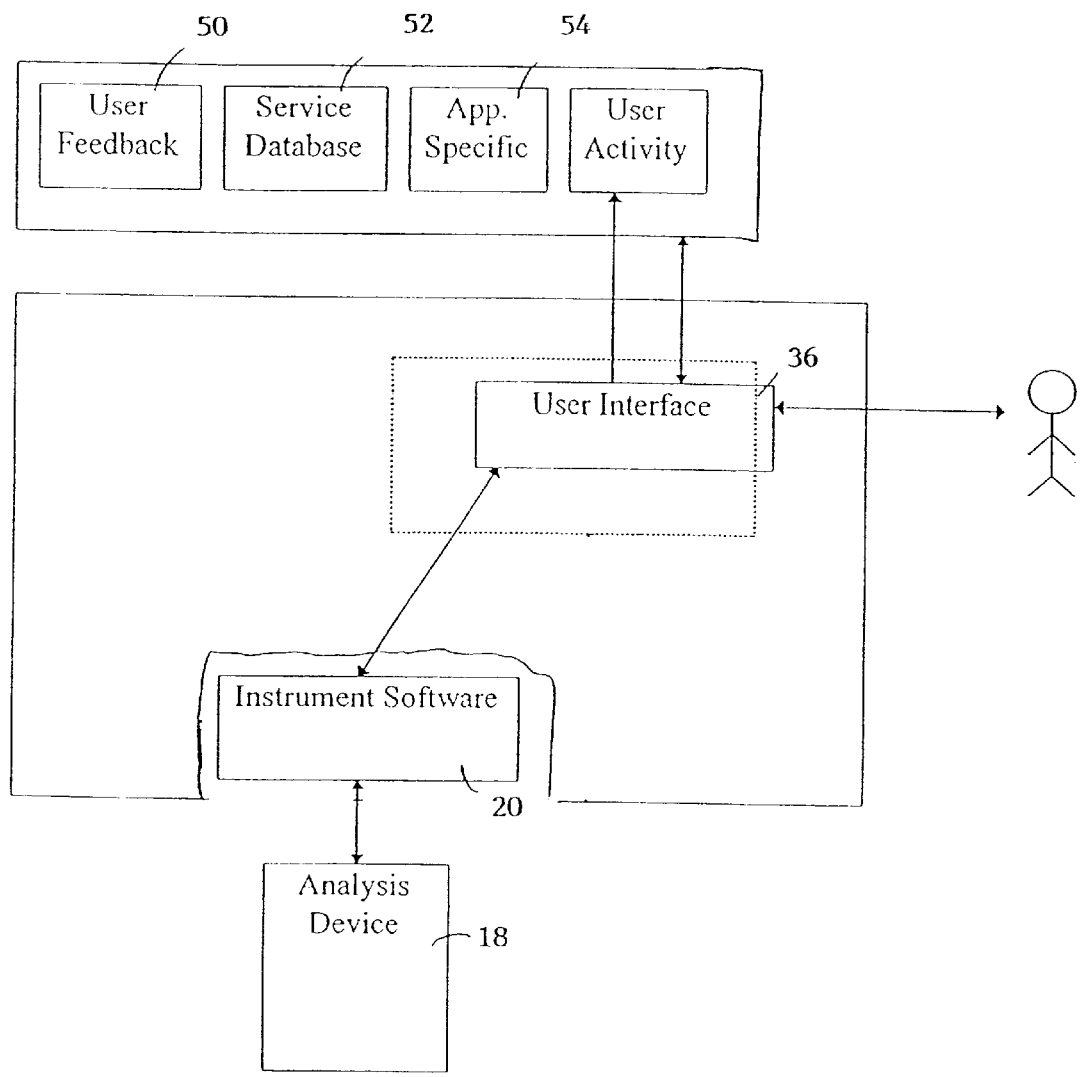
FIG. 7 illustrates examples of user databases according to the present invention.

In a preferred embodiment, the system of the present invention includes one or more user databases which are accessible through the system management software by the user, as shown in FIG. 7. These databases can include, but are not limited to, the following types of databases. A user feedback database 50 will include any complaints by the user, information on the performance of new products after review by the user, any new features or products which have been requested by the user, and any other comments the user might have. A service database 52 would contain information on all service activities performed under the system of the present invention, including those performed by service personnel and those performed directly by the hardware monitoring agent. An application specific database 54 will contain scientific information for each application or type of analysis performed on the analysis device. All user databases could be implemented using such software as Lotus Notes.

Figure 8:
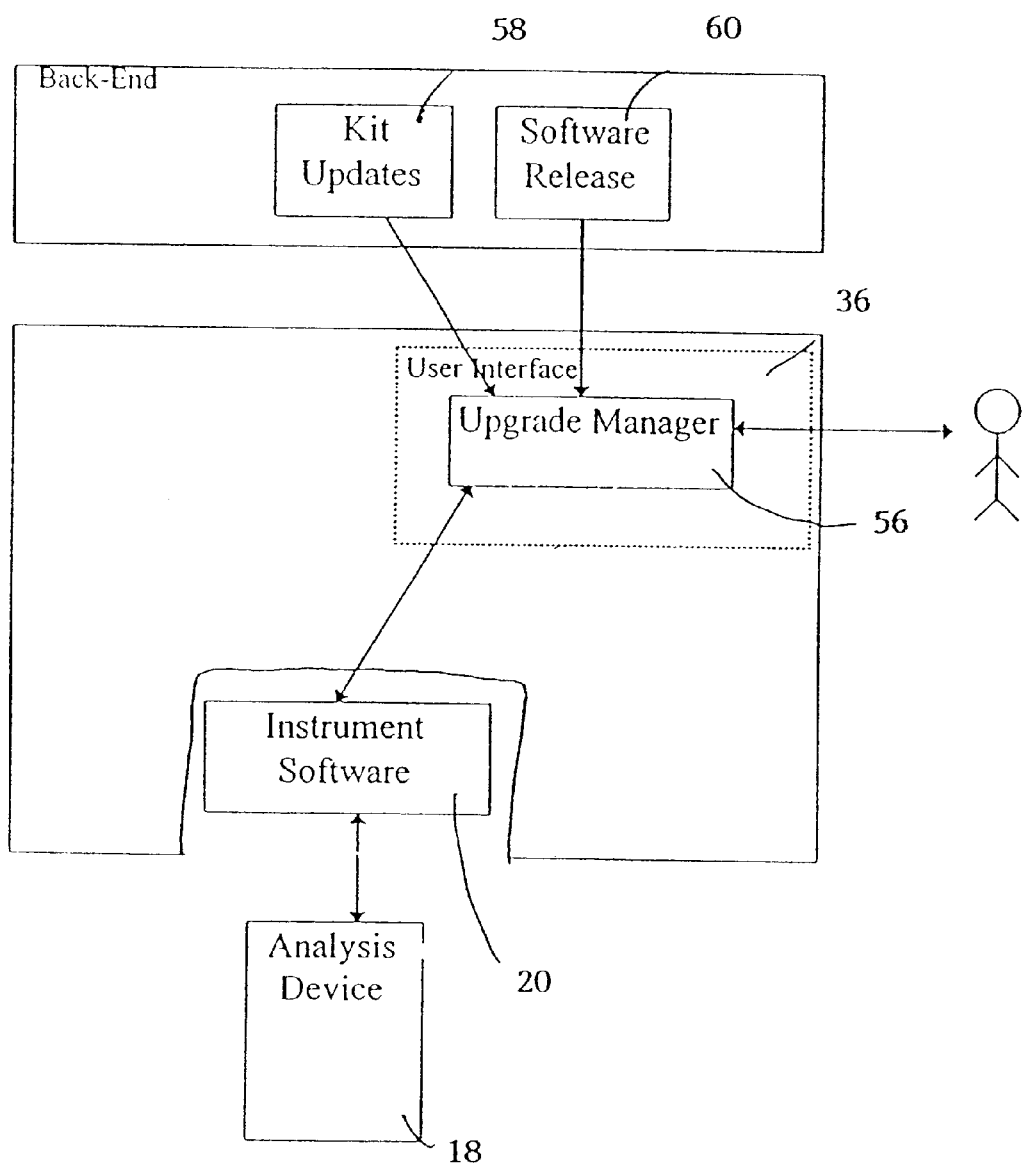
FIG. 8 schematically diagrams an example of a software upgrade manager according to the present invention.

In another preferred embodiment, the system of the present invention includes an upgrade manager as shown in FIG. 8. An upgrade manager 56 is accessible to the user through user interface 36 as shown. Upgrade manager 56 can be manually controlled by the user, or can automatically or semi-automatically perform its functions. One function of upgrade manager 56 is to receive any updated information about analysis device 18, such as the amount of a particular reagent which should be added to the sample for analysis. This updated information is received from a kit update device 58. A software release device 60 can also give the latest upgraded software, or any new software, to upgrade manager 56. Upgrade manager 56 can then download the updated information or software to instrument software 20.

It will be appreciated that the above descriptions are intended only to serve as examples, that many other embodiments are possible within the spirit and the scope of the present invention.

What is claimed is:

1. A system for controlling an analysis device, comprising:
   (a) an instrument software for operating the analysis device; and
   (b) a system management software for receiving a report of a state of the analysis device from said instrument software and for determining a response to said report, said response including a command to alter at least one operating parameter of the analysis device, said system management software including:
      (i) a hardware monitoring agent for interacting with said instrument software to obtain said report; and
      (ii) an expert system software for determining if said report is of an instrument error state, and for recommending an error correction response if said report is of said instrument error state,
   wherein said command is sent to said instrument software by said hardware monitoring agent and is executed by said instrument software; and
   wherein the analysis device is adjusted by altering an operating parameter related to a gain of a lamp.

* * * * *